(12) United States Patent
Nace

(10) Patent No.: US 7,608,051 B1
(45) Date of Patent: Oct. 27, 2009

(54) OSTEOARTHRITIS KNEE ORTHOSIS

(76) Inventor: Richard A. Nace, AP151 C.O. 6151, Centro Co., Santa Anna 2000, San Jose (CR)

( * ) Notice: Subject to any disclaimer, the term of this patent is extended or adjusted under 35 U.S.C. 154(b) by 301 days.

(21) Appl. No.: 11/556,557

(22) Filed: Nov. 3, 2006

(51) Int. Cl.
*A61F 5/00* (2006.01)
(52) U.S. Cl. .................. 602/16; 602/1; 602/5; 602/23; 602/26
(58) Field of Classification Search ............ 602/1, 602/5, 23, 26, 16
See application file for complete search history.

(56) References Cited

U.S. PATENT DOCUMENTS

| | | | |
|---|---|---|---|
| 4,991,571 A * | 2/1991 | Kausek | 602/16 |
| 5,330,418 A * | 7/1994 | Townsend et al. | 602/26 |
| 5,372,576 A | 12/1994 | Hicks | |
| 5,558,628 A | 9/1996 | Bzoch | |
| 5,718,671 A | 2/1998 | Bzoch | |
| 5,895,366 A | 4/1999 | Bzoch | |
| 6,039,709 A | 3/2000 | Bzoch | |
| 7,060,045 B2 * | 6/2006 | Mason et al. | 602/5 |
| 2003/0144620 A1 * | 7/2003 | Sieller et al. | 602/5 |
| 2003/0149386 A1 * | 8/2003 | Ceriani et al. | 602/16 |
| 2005/0240135 A1 * | 10/2005 | Hoffmeier et al. | 602/26 |

* cited by examiner

*Primary Examiner*—Patricia M Bianco
*Assistant Examiner*—Tarla R Patel
(74) *Attorney, Agent, or Firm*—James E. Larson

(57) ABSTRACT

A polycentric hinge is positioned on one side of the patient's knee and a unicentric hinge is positioned on a second side of the knee. A lower portion of the polycentric and unicentric hinge is attached to a knee cuff about a lower leg of the patient. An upper arm of the polycentric and unicentric hinge is attached to a thigh cuff, the upper arm of the unicentric hinge being longer than the upper arm of the polycentric hinge. The upper arm of the unicentric hinge has a 15° to 20° set back angle when the patient's leg is straight. The polycentric hinge has a slotted central plate with star gears engaging a back portion and multiple movable blocks mounted in screw holes on a front edge of the slotted plate supporting an elastic band having a fulcrum point on the polycentric hinge at a lower and upper end.

20 Claims, 12 Drawing Sheets

OSTEOARTHRITIS KNEE ORTHOSIS

FIELD OF THE INVENTION

The invention relates to knee braces. More particularly, it refers to an offset double upright knee brace.

BACKGROUND OF THE INVENTION

Orthotic devices and appliances commonly referred to as "orthotics," have been utilized for many years by orthotists, physical therapists, and occupational therapists to assist in the rehabilitation of patient's joints and associated limbs or adjacent skeletal parts of the patient's body.

Webster's New College Dictionary defines "orthotics" as a branch of mechanical and medical science that deals with the support and bracing of weak or ineffective joints or muscles.

Orthotics or limb braces have been designed to support and protect the joint, alleviate pain associated with joint movement, and to rehabilitate the joint over time with orthotic use.

Primary osteoarthritis is usually related to aging. With aging, the water content of the cartilage increases and the protein makeup of the cartilage degenerates. Repetitive use of the joints over the years can irritate and inflame the cartilage, causing joint pain and swelling. Eventually, cartilage begins to degenerate by flaking or forming tiny crevasses. In advanced cases, there is a total loss of cartilage cushion between the femur and tibia bones at the knee joint, leading to diminished joint space on the affected side of the knee resulting in pain and limitation of joint mobility. Inflammation of the cartilage also can stimulate new bone outgrowths (spurs) to form around the joints causing increased pain and joint inflammation.

Osteoarthritis is often described as "wear and tear" arthritis, as it is highly correlated to age. Osteoarthritis is one of the most frequent causes of physical disability among adults. More than 20 million people in the US have the disease. By 2030, 20 percent of Americans, about 70 million people, will have passed their 65th birthday and will be at risk for osteoarthritis.

Osteoarthrosis is a condition where the joint is affected by degeneration. Osteoarthritis implies the same meaning, but the "itis" adds the meaning that the joint is inflamed. The two terms are often used interchangeably.

Joint replacement surgery of the knee is the surgical treatment for osteoarthrosis or osteoarthritis. It is best to delay knee joint replacement surgery as long as possible, as a total knee replacement may need to be replaced in ten to twenty years. It is a major surgery which requires considerable rehabilitation therapy to restore full function.

Exercise, weight loss if needed, and the use of anti-inflammatory medications and analgesics are often prescribed to assist the patient in managing the pain associated with osteoarthritis. Minimizing the progression of the damage to the cartilage of the knee joint and preventing the formation of bone spurs from "bone on bone" during knee joint bending is an important part of patient care.

The actual pain of osteoarthritis or osteoarthrosis comes from wearing away of the soft cartilage that pads the junction of the femur (upper leg bone of the knee) and the tibia (lower leg bone of the knee). With irritation of the joint, bone spurs can form causing bits of bone and cartilage to break off which float inside the joint space further irritating the knee. The most common form of osteoarthritis or osteoarthrosis is unicompartmental, meaning that only one of the three compartments of the knee joint are significantly affected by the loss of cartilage padding. The medial compartment of the knee is on the inside of the center line of the body. The lateral compartment of the knee is on the outside plane of the body, and the patellar compartment is in the center top of the knee behind the patella or knee cap. The majority of cases of osteoarthritis are medial compartment degeneration where the cartilage or cushioning of the knee joint has significantly deteriorated. The knee then becomes imbalanced, with the knee bowing outwards. This is often called a "bowleg" condition. A "bowleg" (genu varum), commonly referred to as a valgus deformity of the knee joint, places significant force on the medial compartment of the knee, which aggravates the pain associated with osteoarthritis when the patient walks, bends the knee, or stands up.

As the cartilage or padding of the knee joint on the lateral compartment cartilage is worn away, the knee will deform abnormally bending inwards at the knee joint giving the patient a knock kneed appearance. This is referred to as a varus deformity of the knee joint.

Osteoarthritis knee braces are designed to do two things: first, correct the abnormal bending of the knee joint inwards or outwards (varus or valgus correction). Secondly, many osteoarthritis knee orthotics or braces are designed to prevent the "bone on bone" contact of the femur and tibia bones in the medial or lateral compartment of the knee joint as the patient bears weight during ambulation. This action of lifting femur, pulling down the tibia or keeping the femur and tibia bones from coming in contact during the straightening of the knee during heel strike is often called "unloading" the knee joint. By "unloading" the knee joint, the constant irritation of the degenerated cartilage in the affected compartment of the knee (medial or lateral) can lead to a significant reduction in pain and further injury to the knee joint. Osteoarthritis knee braces also provide improved alignment of the upper and lower aspects of the knee joint by preventing the bending inwards or outwards of the knee joint during gait. These two features, unloading and alignment are provided by most of the osteoarthritis knee orthotics available in today's market.

The majority of knee orthotics available to treat osteoarthritis of the knee utilizes a single upright attached to an upper thigh cuff and lower shin cuff. The upright is located on the side of the collapsed compartment of the knee; i.e. medial side for medial compartment osteoarthritis. The attached cuffs "offload" the biomechanical force on the affected compartment of the knee by increasing the joint space on the affected side as the knee goes from flexion to extension. Many osteoarthritis braces use an angled strap from the upper part of the brace that goes across the opposite side of the knee joint from the side bar or upright to improve the alignment of the knee during ambulation to better balance the forces on the knee during gait more evenly. The strap provides a three point leverage that pulls the knee joint into proper alignment during gait. A combination of the single sided upright with cuff attachments and the valgus producing strap have shown to provide improved performance in severe genu varum osteoarthritis. However, it is difficult to set the desired degrees of flexion and extension.

Although many of the existing knee braces containing locking hinge assemblies serve their intended purpose, difficulty in ease of setting the desired degrees of flexion and extension continues to be a problem.

SUMMARY OF THE INVENTION

The present invention provides an osteoarthritis knee orthosis easily fabricated in a wide range of sizes for either knee (left or right) to treat either medial or lateral (varus or valgus) unicompartmental degeneration of the knee joint caused by osteoarthritis or osteoarthrosis with easily managed controls for setting the desired degree of flexion and extension. The knee orthosis of this invention will unload the pressure on the affected side of the knee joint, provide balanced joint space on both sides of the knee during ambulation, improve knee joint alignment, and can be adjusted as the condition of the knee improves or deteriorates to maintain joint space balance, an unloading effect on the affected side of the knee joint, and improved knee joint alignment during gait.

As alignment of the knee changes (joint space balance), the mechanism of the knee brace is adjusted by this invention so that joint space balance is continually maintained with joint rehabilitation. The current invention achieves this significant improvement with an adjustable dynamic fulcrum to allow the clinician to quickly and easily adjust the brace to maintain joint space balance as needed during the knee rehabilitation process.

The present invention accomplishes the desired result of joint space balance by providing a lateral polycentric hinge and a medial unicentric hinge component positionable respectively laterally and medially adjacent the knee joint. A rigid cuff is circumscribable about the front of the lower leg. The lower member of each hinge is attached to a lateral and medial upright element respectively integral with the rigid cuff. A semi-rigid thigh cuff is aligned with the back of a patient's thigh, above the knee joint. The thigh cuff has a lateral and medial element extending downwardly to engage a top hinge arm of the lateral and medial hinge respectively. The top medial hinge arm is longer than a corresponding top lateral hinge arm. The top medial hinge arm is fixed at a posterior angle of about 15° to 20° in full knee extension. A spring loaded adjustable fulcrum polycentric lateral hinge component is used to assist during leg extension-flexion during walking, squatting and sitting. By moving setting blocks different degrees of tension is introduced into the polycentric lateral hinge.

BRIEF DESCRIPTION OF THE DRAWINGS

This invention can be best understood by those having ordinary skill in the art by reference to the following detailed description, when considered in conjunction with the accompanying drawings in which.

DETAILED DESCRIPTION OF THE INVENTION

Figure 1:
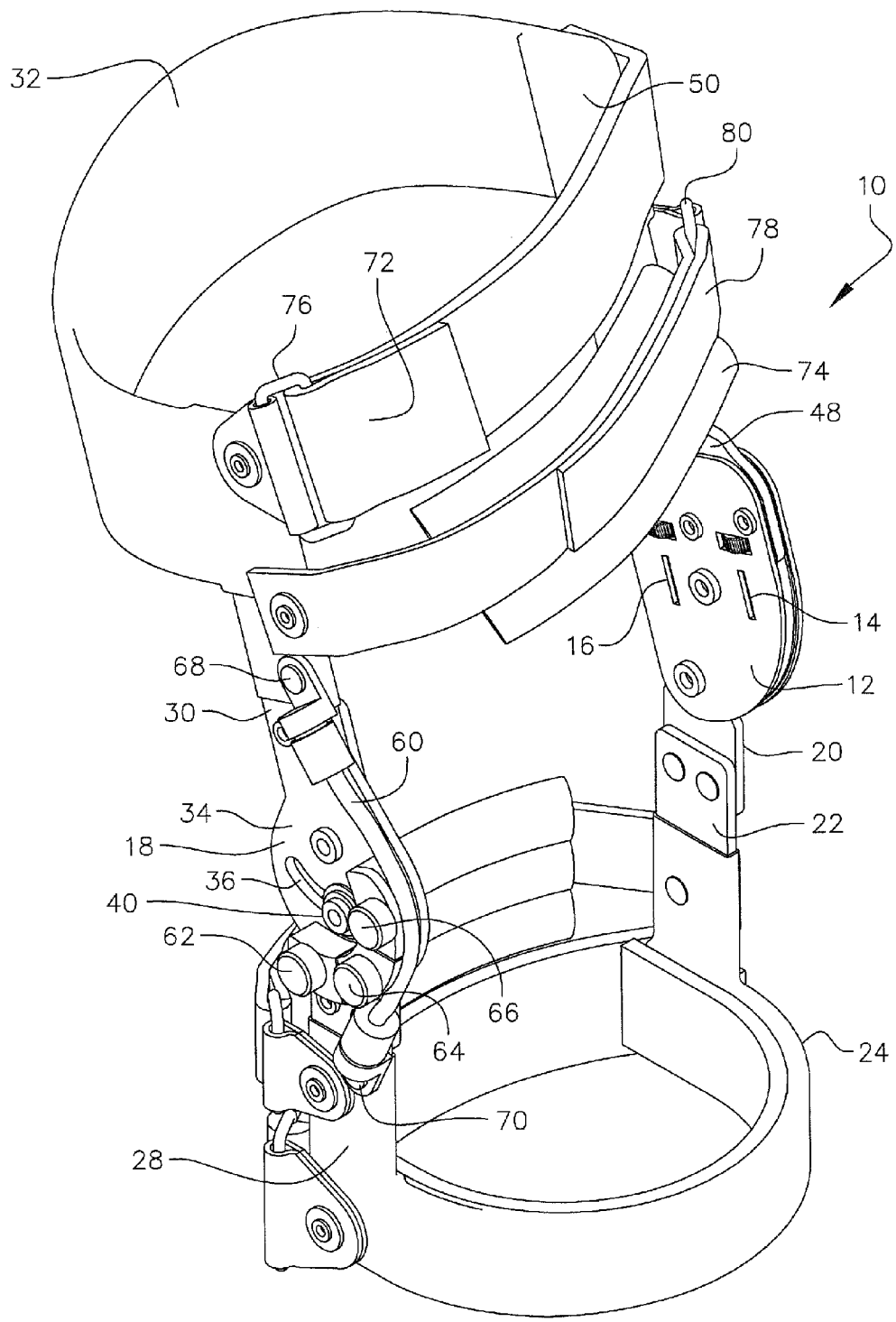
FIG. 1 is a lateral side perspective view of the hinge assembly of this invention including the attachment strapping.

Throughout the following detailed description the same reference numerals refer to the same elements in all figures.

Figure 2:
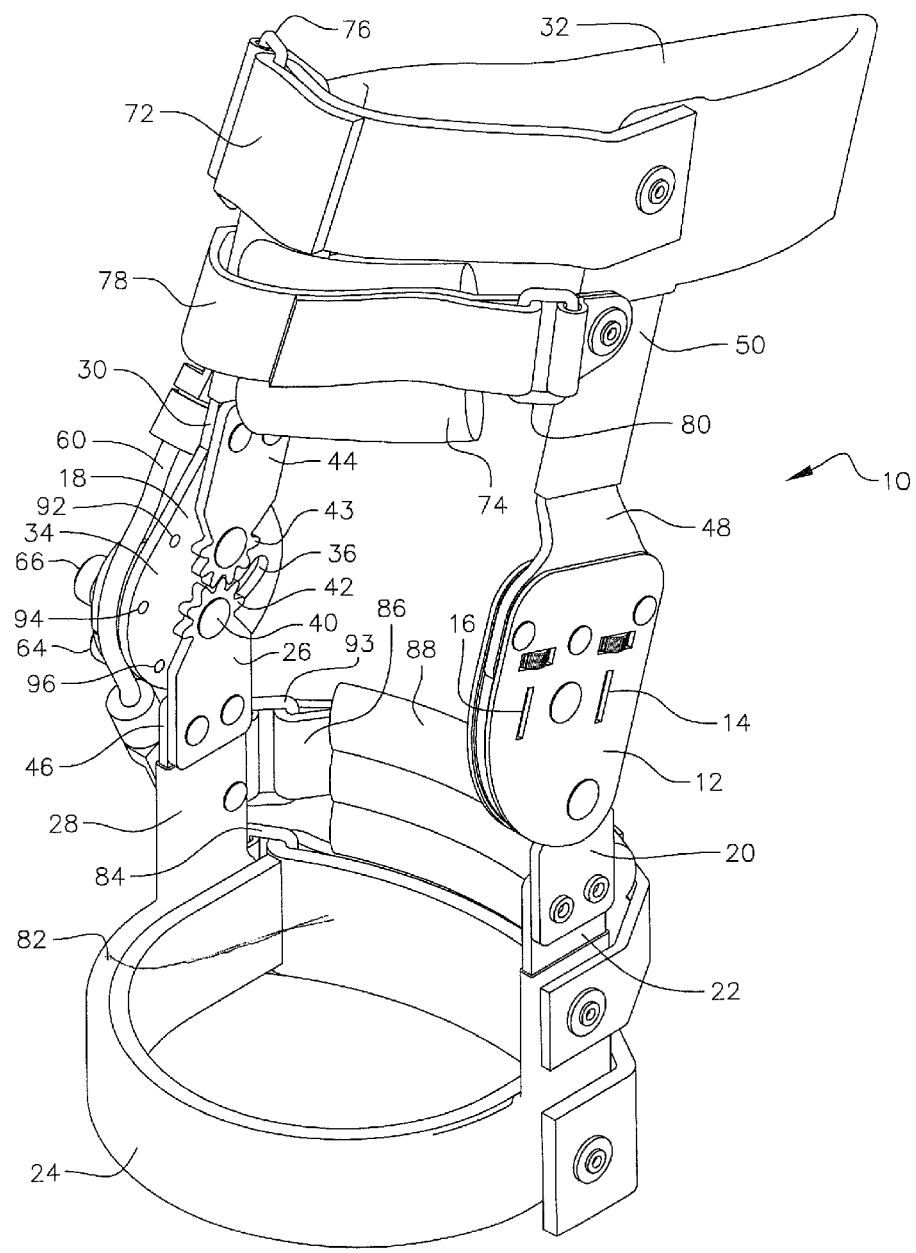
FIG. 2 is a medial side perspective view of the hinge assembly of FIG. 1.
Figure 3:
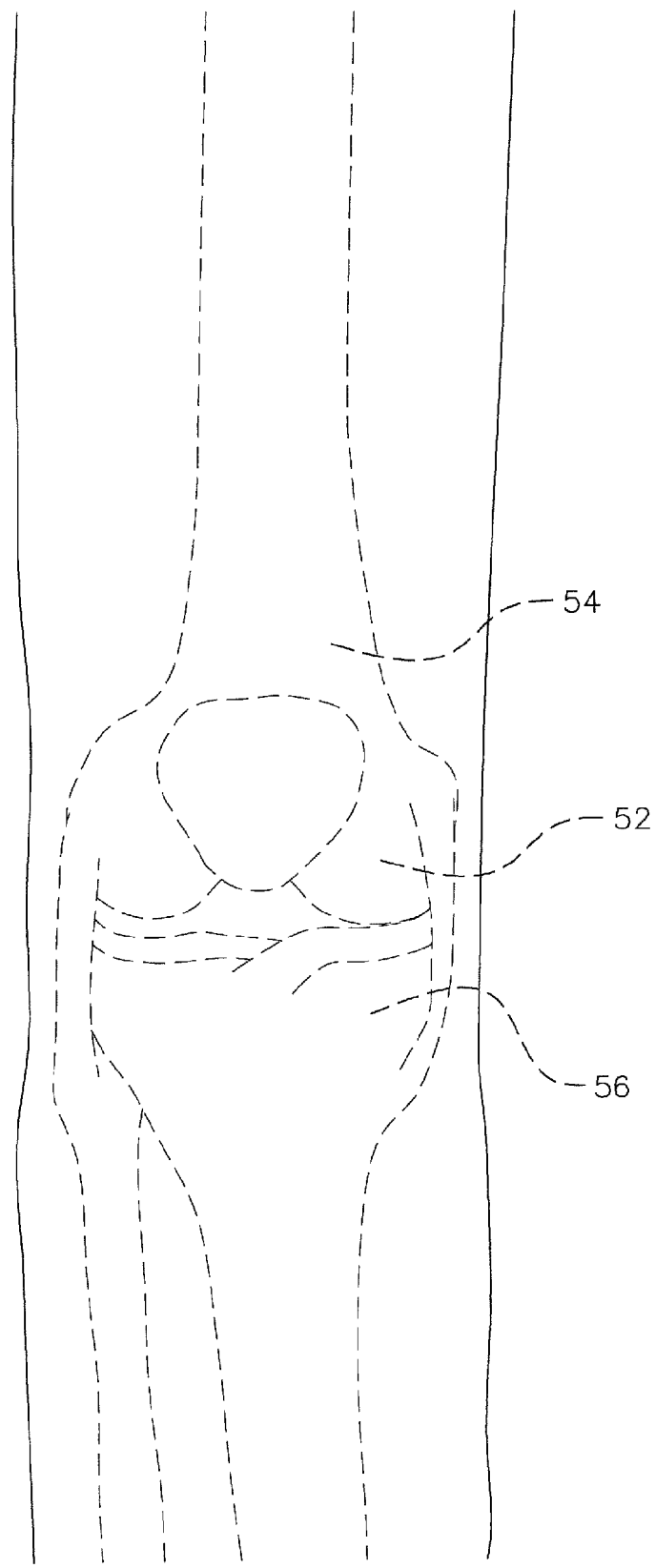
FIG. 3 is a front view of a knee with a hidden view of the patella out of alignment.

Referring to FIGS. 1 and 2, the osteoarthritis knee orthosis 10 (hereafter identified as OA), has a medial unicentric hinge 12 with flexion stop 14 and extension stop 16 at any setting. The medial unicentric hinge 12 is substantially parallel to a lateral polycentric adjustable tension offloading hinge 18. The bottom end 20 of medial hinge 12 is attached to a first upright member 22 integral with a rigid knee ring 24. A lower gear plate 26 of lateral hinge 18 is attached to a second upright member 28 integral with knee ring 24.

An upper arm 30 of the lateral hinge 18 connects at an upper end to a semi-rigid upper thigh cuff 32. A lower portion of the lateral hinge broadens out to a slotted hinge connector plate 34. A slot 36, in connector plate 34 contains a transverse shaft on rivet 40. The rivet 40 attaches a first star gear 42 to an inside surface of the slotted connector plate 34. A second star gear 43 is integral with a gear plate 44 attached to an inner surface of upper arm 30.

Figure 4:
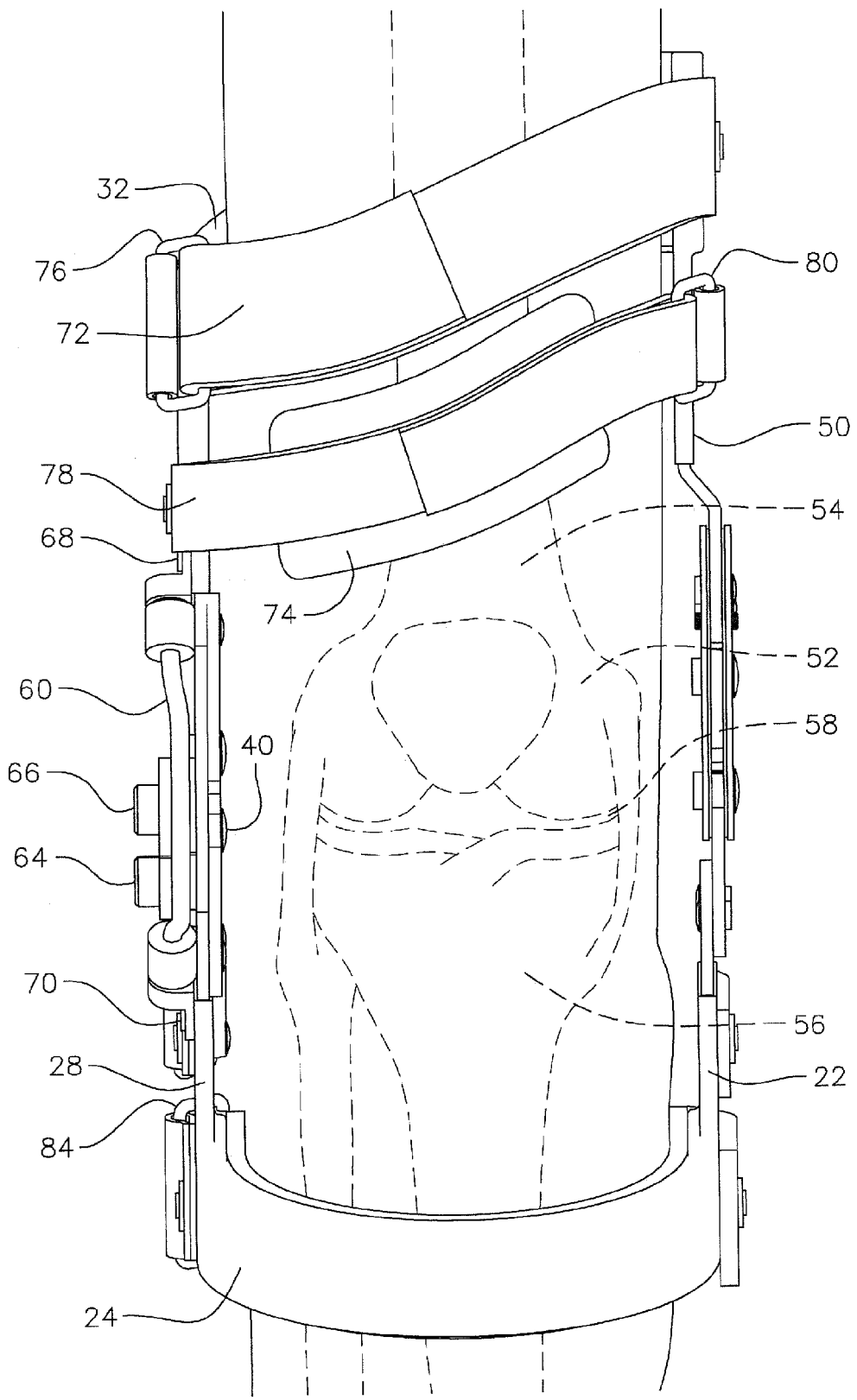
FIG. 4 is a front view of a knee with a hidden view of the patella with the knee brace of this invention in place.

An upper arm 48 of the medial hinge 12 is attached at its top end 50 to the semi-rigid upper thigh cuff 32. Medial hinge 12 is a KWIK-SET design set forth in U.S. Pat. No. 6,039,709, incorporated herein by reference. The upper arm 48 of medial hinge 12 is significantly longer than the upper arm 30 of the lateral hinge set 18; about 1½ inches in the medium size. The longer length of medial upper arm 48 compared to the upper arm 30 of the lateral hinge 18 encourages unloading of force from the medial compartment of the knee by lifting the medial side 52 of the femur 54 off of the tibia 56 with weight bearing during full leg extension. See the gap 58 shown in FIG. 4.

The lower medial side upright 22 and lower lateral side upright 28 are equivalent in length. The medial upper arm 48 is set back at an angle of approximately 15° to 20° with the leg straight whereas upper lateral arm 30 and lower lateral upright 28 are in a relatively straight alignment with the hinge when the leg is straight. The offset portion of arm 48 improves knee alignment from 20° of flexion to full extension of the knee joint and prevents "reverse Screw Home Mechanism" rotation of the knee.

As shown, the various elements are held together by rivets such as rivet 40. Other equivalent means of attachment could be substituted for the rivets.

Figure 5A:
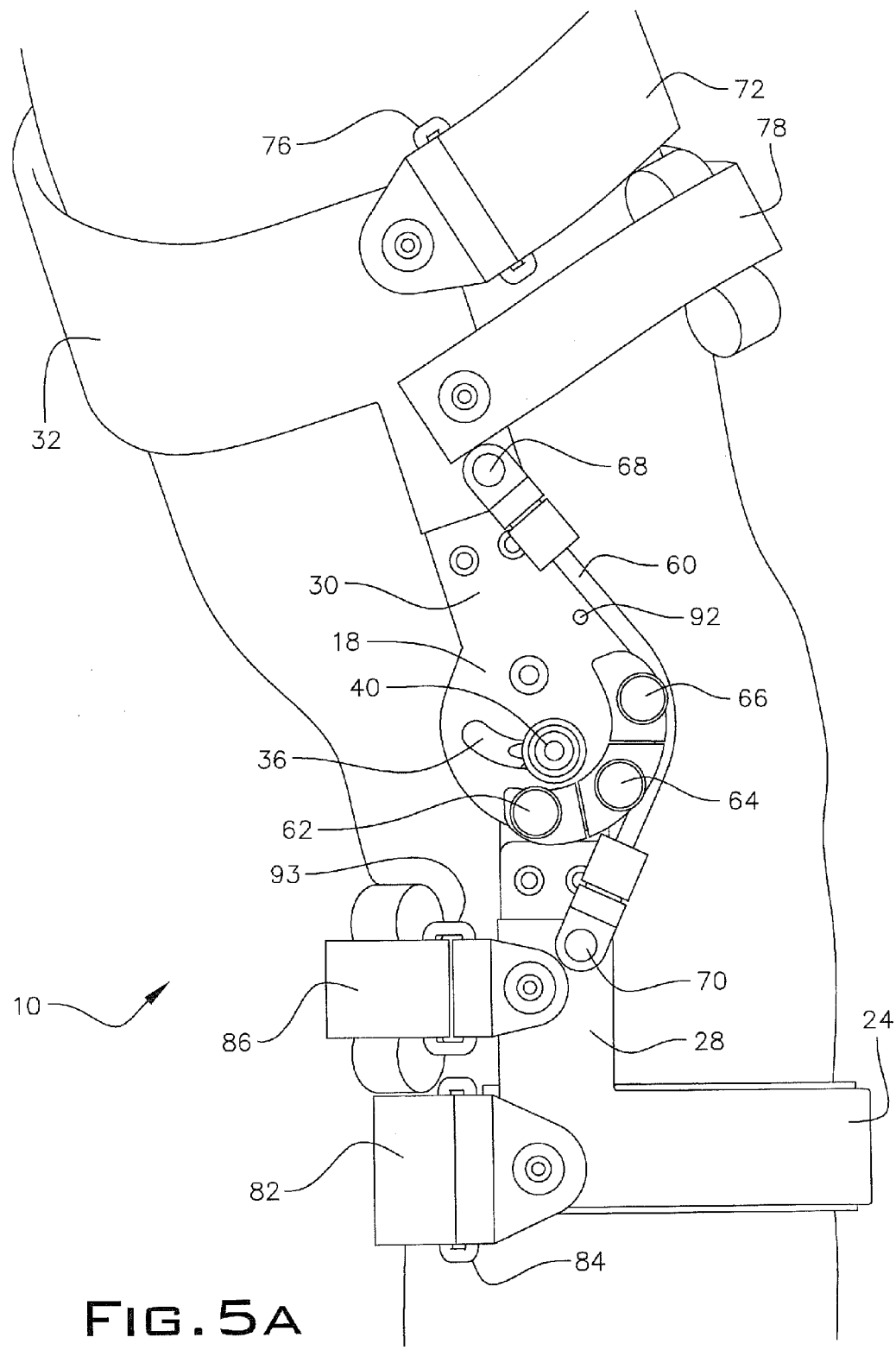
FIG. 5A is a lateral side view of the hinge assembly of FIG. 1 on an extended leg of a patient.
Figure 5B:
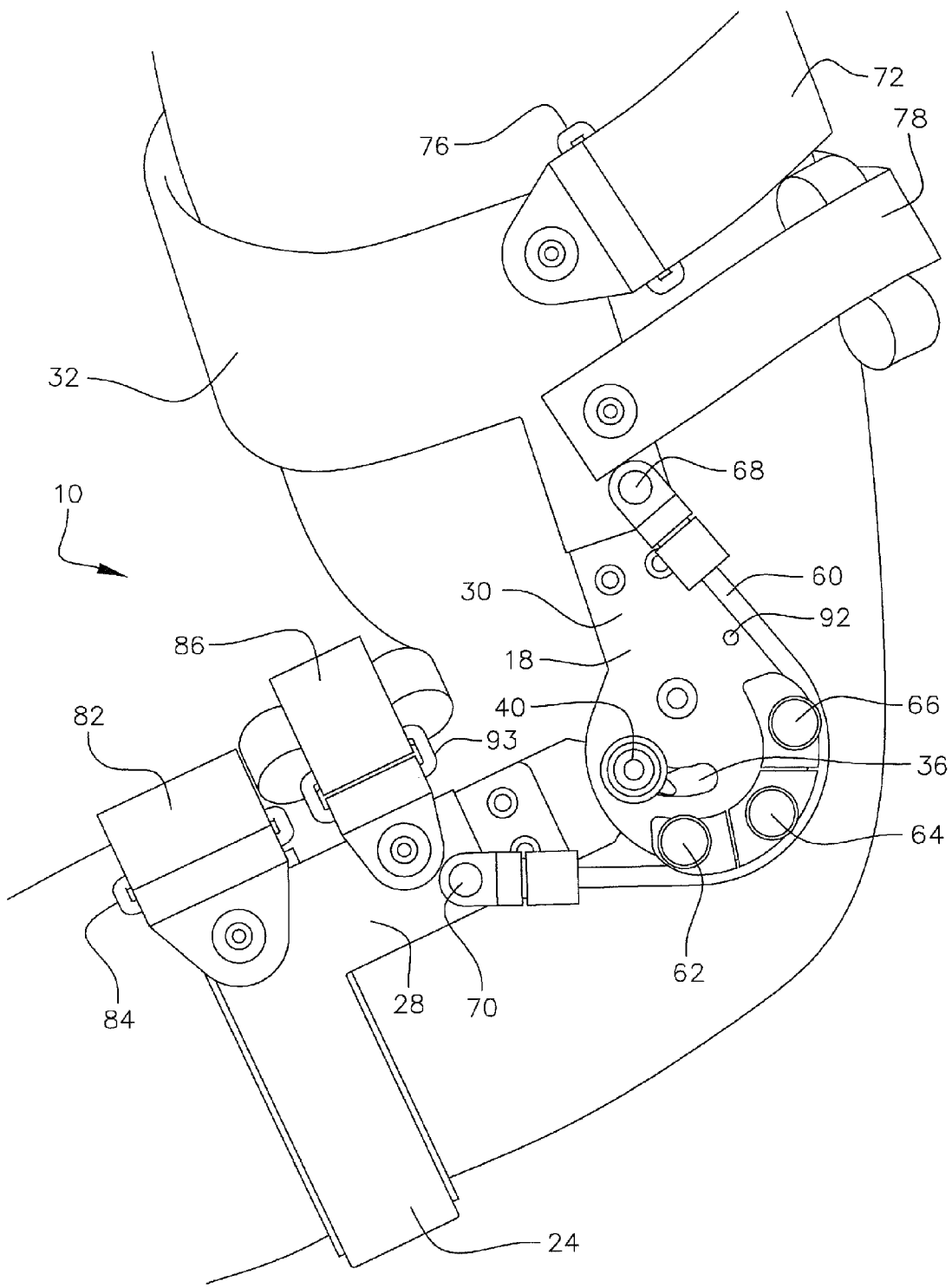
FIG. 5B is a lateral side view of the hinge assembly of FIG. 5A with the patient's knee in a bent position.

On polycentric hinge 18, an elastic band 60 attaches at a lower end on the outside of the second upright member 28 at fulcrum point 70 and travels adjacent adjustable dynamic fulcrum setting blocks 62, 64 and 66 to terminate at fulcrum 68. The dynamic tension of the fulcrum 68 can be set by the fitter by using fulcrum blocks 62, 64 and 66. In addition, various elastic bands 60 with varying elastic properties can be substituted to allow the fitter to adjust the dynamic fulcrum with multiple tension forces. The dynamic adjustable fulcrum is derived from the band 60 positioned from the lower fulcrum point 70, and stretched over blocks 62, 64 and 66 at the lateral hinge as the knee bends. See FIG. 5B. The adjustable dynamic fulcrum is used to provide a dynamic tension force at the knee joint that can be used to balance the joint space 58 between the medial and lateral compartments and to provide optimal alignment of the knee with the OA 10 brace.

Figure 6A:
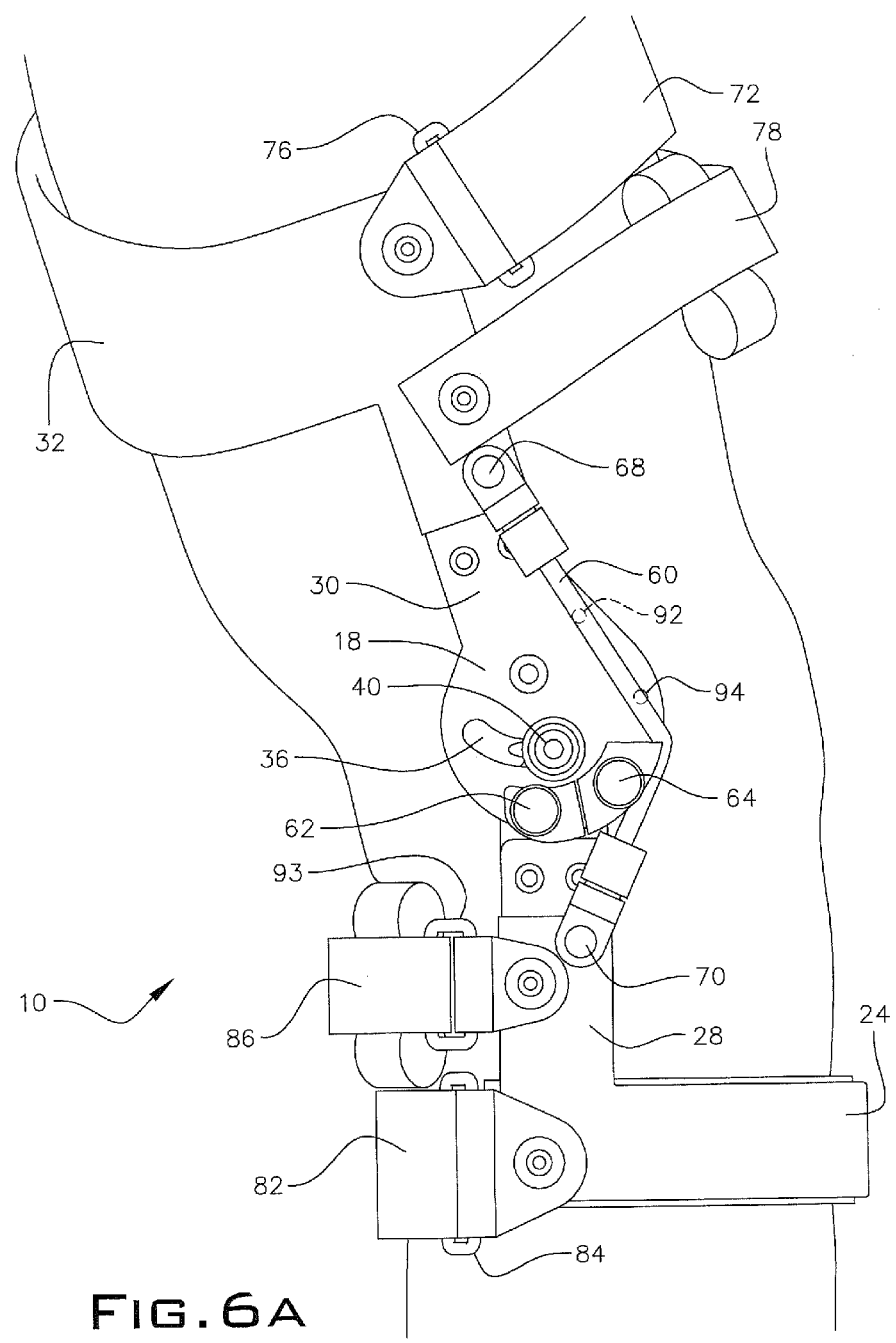
FIG. 6A is a lateral side view of the hinge assembly of FIG. 1 on an extended leg of a patient with only two setting blocks in place.
Figure 6B:
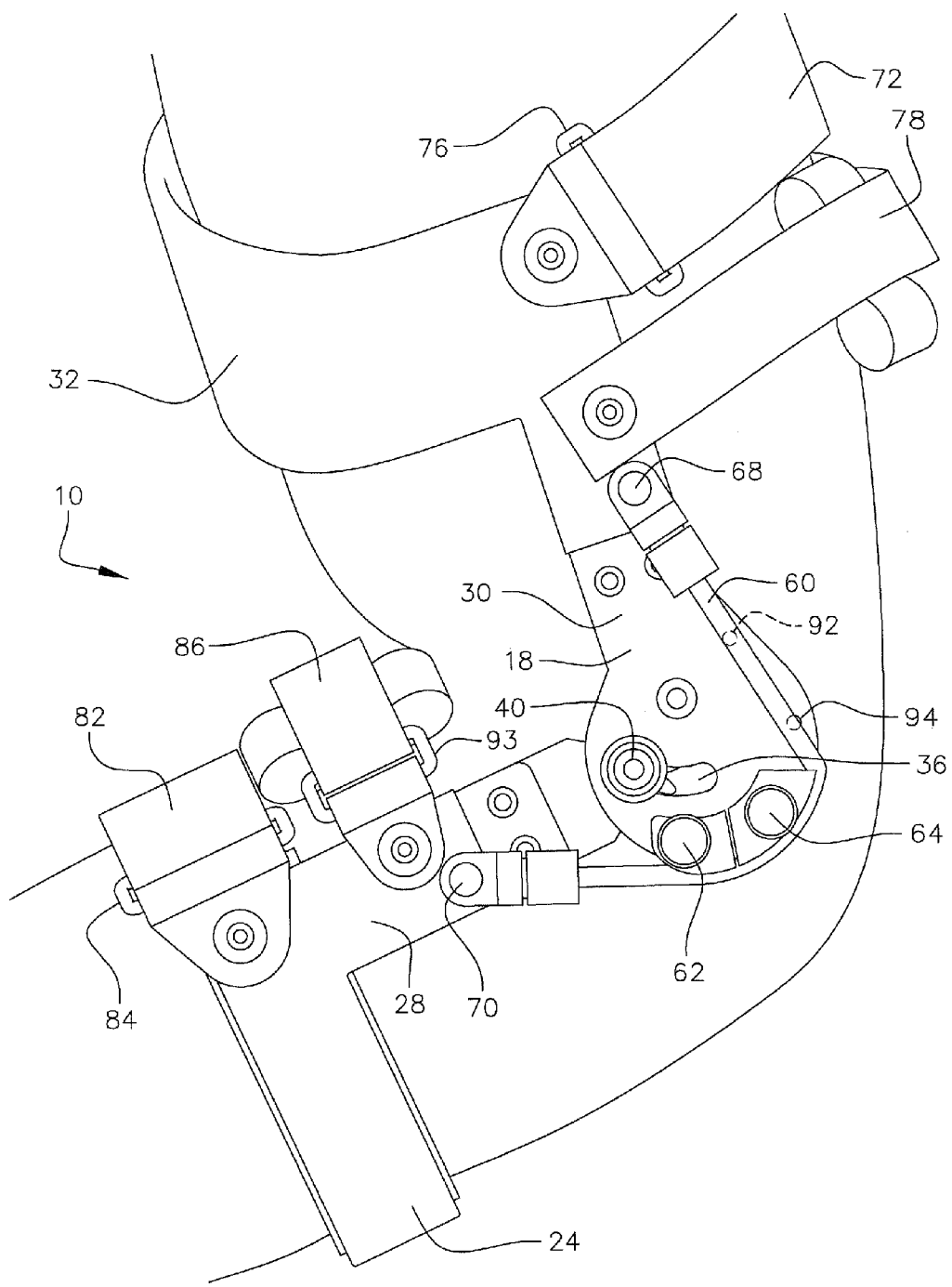
FIG. 6B is a lateral side elevational view according to FIG. 6A with the patient's knee bent.

FIGS. 6A and 6B show alignment using only two blocks, 62 and 64, on the polycentric hinge 18.

Figure 7A:
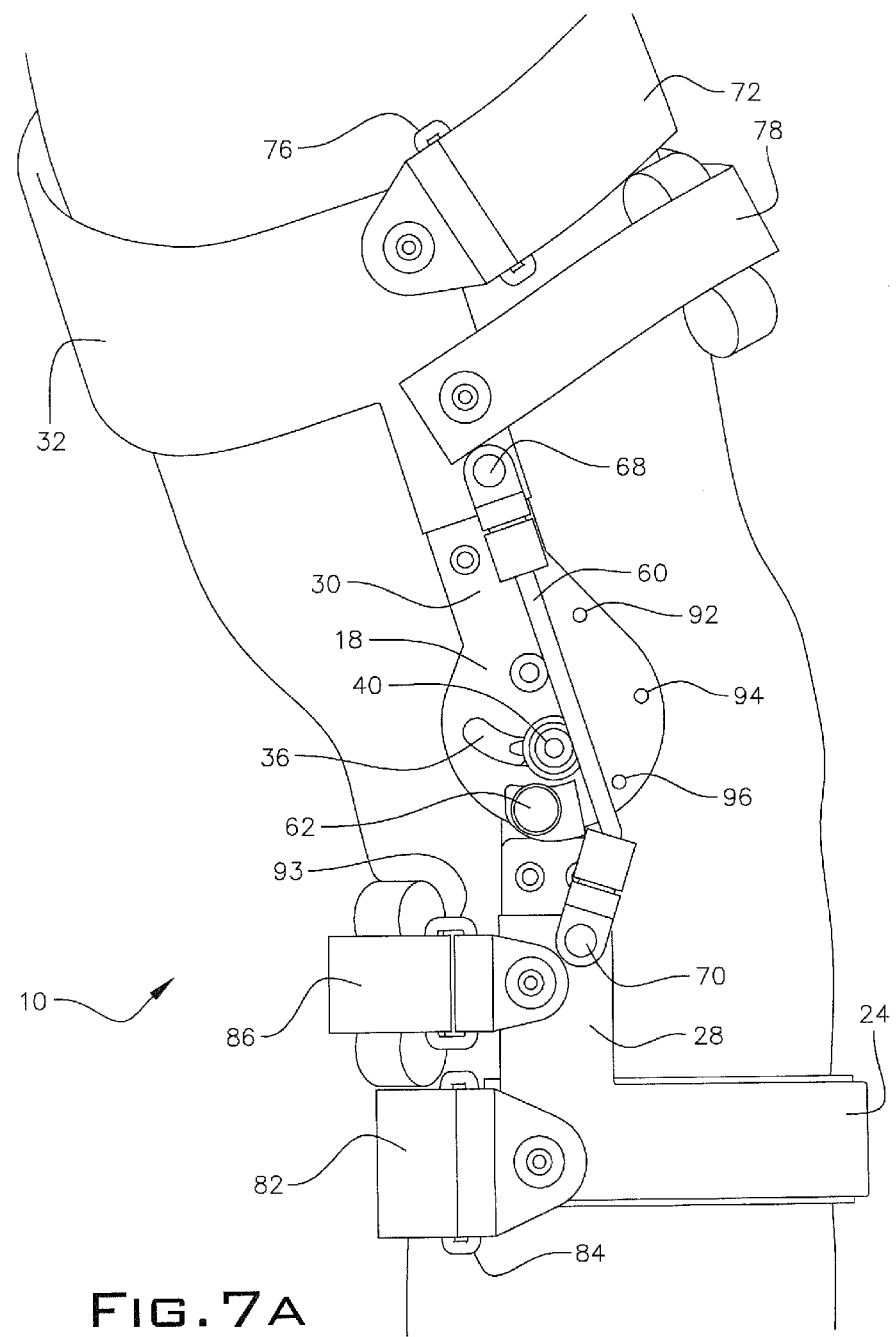
FIG. 7A is a lateral side view of the hinge assembly of FIG. 1 on an extended leg of a patient with only one setting block in place.
Figure 7B:
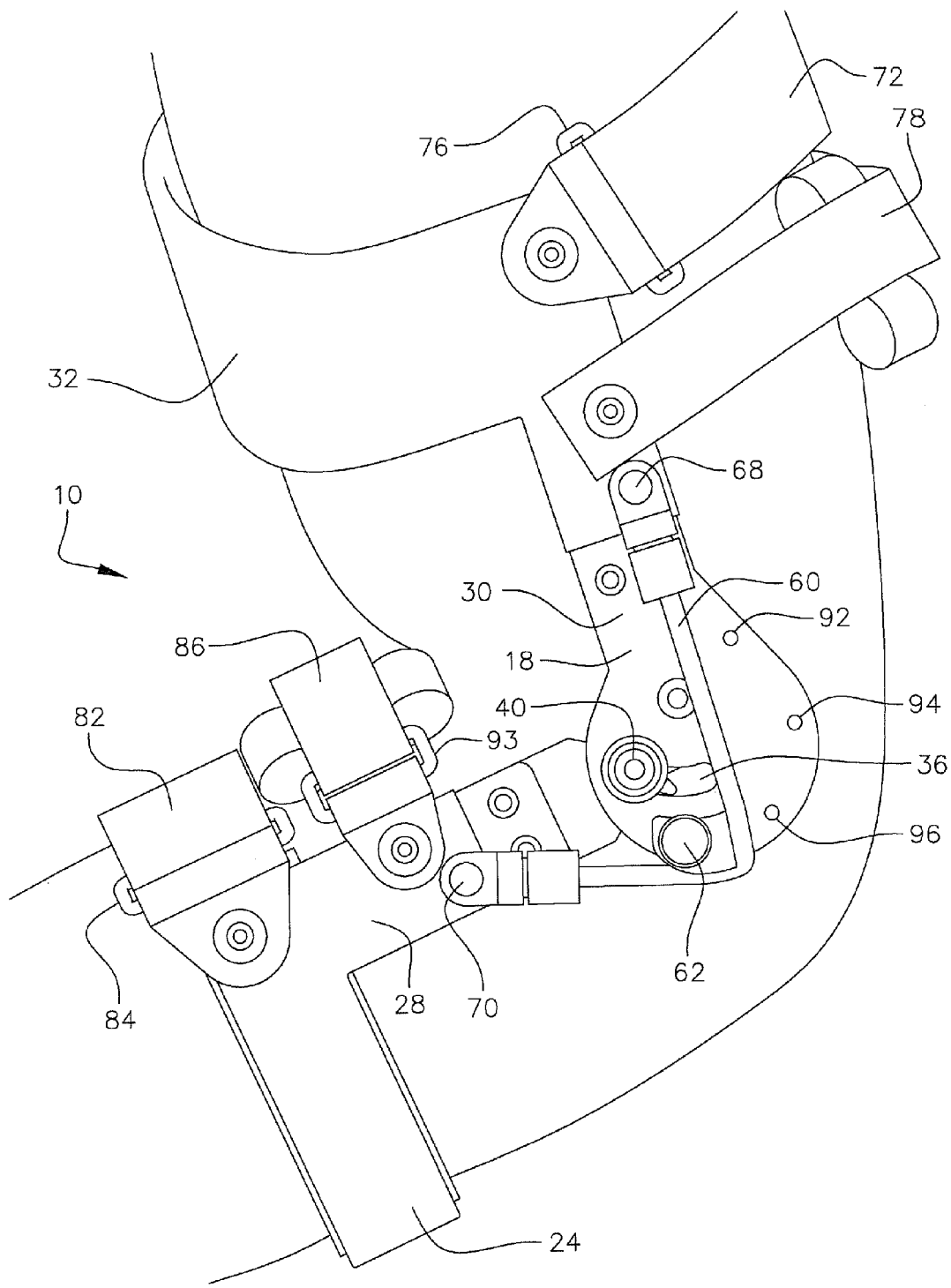
FIG. 7B is a lateral side according to FIG. 7A with the patient's knee bent.

FIGS. 7A and 7B show minimal alignment using only one block 62 on the polycentric hinge 18.

Figure 8A:
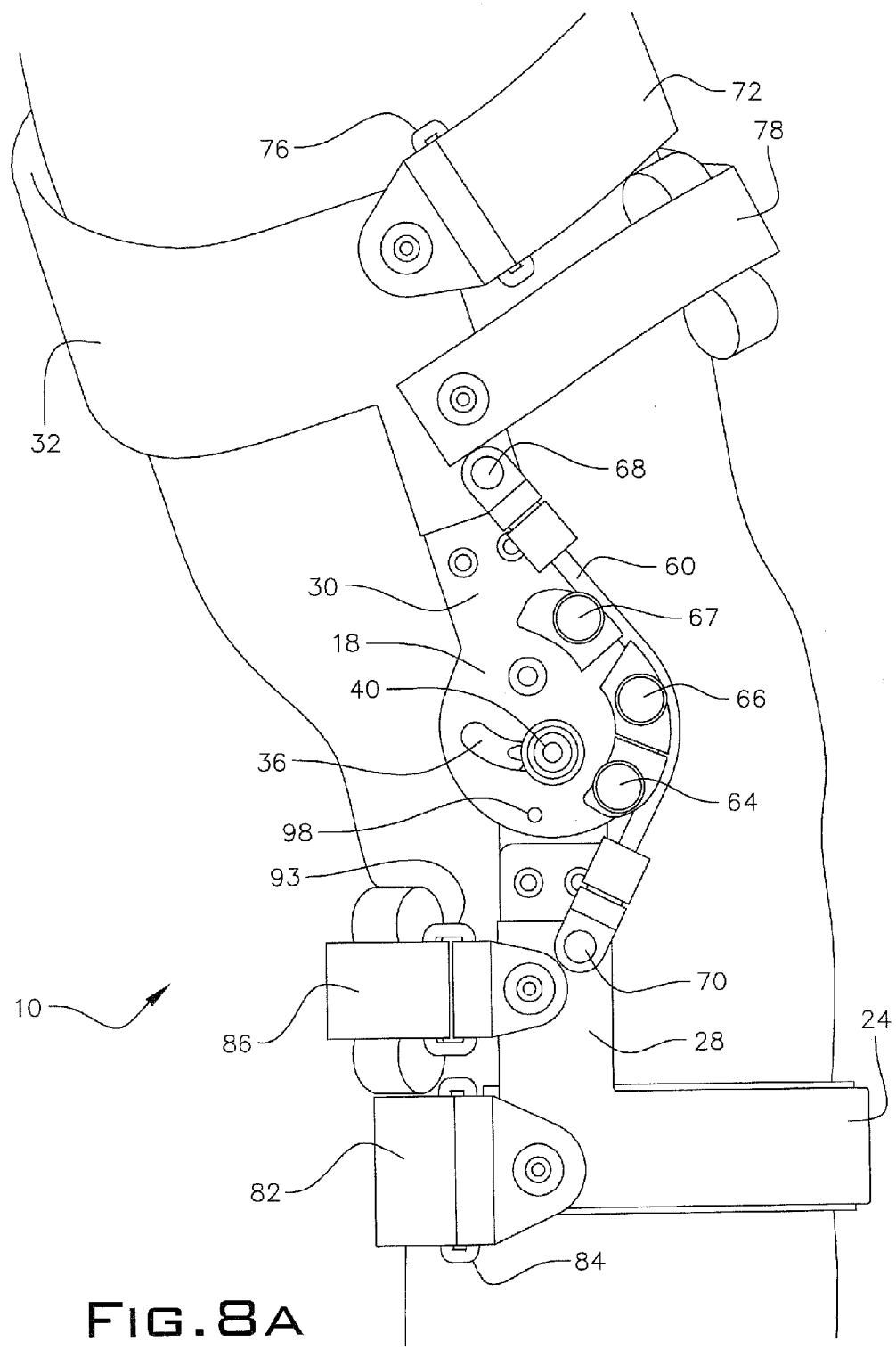
FIG. 8A is a lateral side view according to FIG. 1 on an extended leg of a patient with the setting blocks moved to an extreme position.
Figure 8B:
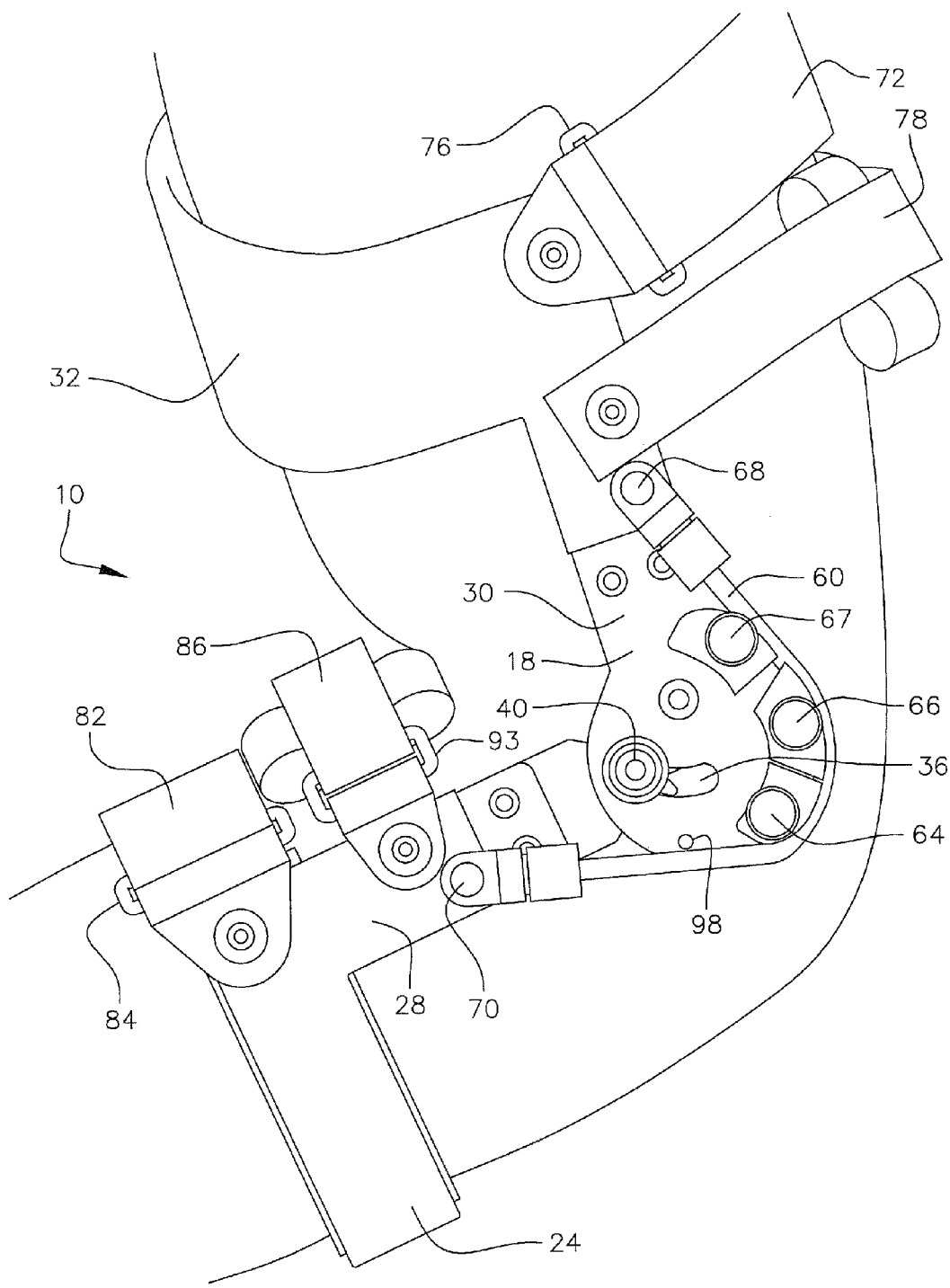
FIG. 8B is a lateral side view according to FIG. 8A with the patient's knee bent.

FIGS. 8A and 8B show an extreme alignment using blocks 64, 66 and 67. In this condition there is no block 62 in lower aperture 98 on the polycentric hinge 18.

A strap 72 tightens thigh cuff 32 in place.

A second mid-thigh cuff securing strap 78 is a soft elastic material with a soft adjustable pad 74 placed at the inner midpoint area of strap 78. Strap 72 is placed through a D-ring fastener 76 on the side of the thigh cuff 72. Hook and loop material is used to engage strap 72 to itself. Soft padded mid-thigh securing strap 78 travels from the lateral side of OA 10 through a second D-ring fastener 80 on the medial side of OA 10. The strap 78 fastens to itself by hook and loop material.

A shin cuff soft elastic material securing strap 82 travels across the back of the patient's calf through a third D-ring fastener 84 on the lower end of the lateral upright 28 and fastens onto itself with hook and loop material. A padded calf strap 86 travels around the back of the calf with an adjustable pad 88 located at mid strap 86. Strap 86 passes through a D-ring fastener 93 on the lower upright 28 and is attached to itself by hook and loop material.

The knee brace bends with free moving axial hinges, each with six equivalently sized axial teeth on the upper and lower aspects of the inner hinge assembly of the medial and lateral hinges 12 and 18. As the knee bends, the bend movement is tracked or guided by the rigid brace uprights at the hinge center axle through groove 36 on the lateral hinge. The hinge alignment forces the bend line of the brace through grooves 36 that is pre-cut into the lateral hinge 18. The specific bend movement of the knee is controlled by the hinge axle traveling through the grooves 36 in the lateral hinge 18. The adjustable dynamic fulcrum on the lateral hinge 18 can be set to provide a dynamic assist mechanism 62, 64 and 66 with spring band 60 to assist in controlling the alignment and movement of the knee from 20° of flexion to full extension of the knee. The adjustable properties of the dynamic fulcrum offer the fitter or wearer multiple settings to maintain knee joint space balance, improved knee joint alignment, and prevention of "reverse Screw Home Mechanism" or controlled rotation of the knee as the knee goes from 20° flexion to extension.

The adjustable dynamic fulcrum band mechanism 60 is on the lateral upright of the OA Knee Brace 10 for medial compartment osteoarthritis. Four threaded holes 92, 94, 96 and 98 are arranged along the hinge of the outer lateral connector plate 34. Blocks 62, 64, 66 and 67 are screwed into the holes as needed. Block 64 can be inserted in hole 96 providing the center point of the elastic band fulcrum as the knee bends if the optimal dynamic setting of the adjustable pull mechanism is needed. A second block 62 with elastic band 60 tracking material can be inserted into threaded hole 98 if another optimal dynamic setting of the adjustable pull mechanism is needed. A third adjustable dynamic fulcrum mechanism is available by inserting block 66 with the elastic band 60 tracking material into threaded hole 94. By providing three or more incrementally stronger or more elastic bands, the fitter will have multiple settings to adjust the dynamic fulcrum to maintain the correct amount of dynamic force to maintain optimal joint space on both the medial and lateral compartments of the knee as well as to maintain optimal knee alignment during the motion of the knee during ambulation.

Other equivalent elements can be substituted for the elements disclosed herein to produce the same results in the same way.

Having thus described the invention, what is claimed for Letters Patent follows:

1. An offset double upright knee brace for treating osteoarthritis comprising:

a lateral polycentric hinge and a medial unicentric hinge positioned laterally and medially respectively, adjacent a knee joint affected by osteoarthritis, the lateral polycentric hinge attached at a lower portion to a lateral upright member integral with a rigid shin cuff adapted to be circumscribable about a patient's anterior lower leg, an upper arm of the lateral polycentric hinge attached to a semi-rigid thigh cuff, adapted to be aligned with a back of a patient's thigh, the lateral polycentric hinge having a slotted plate with an upper first star gear rigidly attached to a back of the slotted plate, and a second star gear movably attached at the back of the slotted plate by a transverse shaft through the slot, multiple threaded holes spaced apart and adjacent a front edge of the slotted plate, corresponding blocks insertable in the threaded holes with an elastic band positioned on a front portion of the blocks with a lower and upper fulcrum point terminating ends of the elastic band on an outside surface of the polycentric hinge, the lateral upright member, the polycentric hinge and the upper arm of the lateral polycentric hinge all defining a first lateral upright of the double upright knee brace;

the medial hinge having an upper arm attached to the thigh cuff, the upper arm of the unicentric hinge being longer than the upper arm of the lateral polycentric hinge, the medial hinge having a bottom end attached to an integral upright member of the rigid shin cuff around the lower leg, the medial hinge having an extension and a flexion setting on a central plate, the integral upright member of the rigid shin cuff, the medial hinge bottom end, the unicentric hinge and the upper arm of the medial unicentric hinge all defining a second medial upright of the double upright knee brace; and the brace offset configuration resulting from the semi-rigid thigh cuff having one side positioned at a height higher than its opposed side, such that the semi-rigid thigh cuff and the rigid shin cuff have different horizontal axis and wherein the upper arm of the unicentric hinge is angled backwardly from a vertical axis of the second medial upright.

2. The offset double upright knee brace of claim 1, wherein there are from one to four blocks supporting the elastic band.

3. The offset double upright knee brace of claim 1, wherein the upper arm of the medial hinge is at least 1½ inches longer than the upper arm of the lateral polycentric hinge.

4. The offset double upright knee brace of claim 1, wherein the transverse shaft through the slotted plate is attached to a rivet.

5. The offset double upright knee brace of claim 1, wherein the semi-rigid thigh cuff is attached to a thigh cuff securing strap by a D-ring.

6. The offset double upright knee brace of claim 5, wherein a mid-thigh securing strap is attached at one end by a rivet to the upper arm of the lateral polycentric hinge and at a second end to the upper arm of the medial unicentric hinge by a D-ring.

7. The offset double upright knee brace of claim 1, wherein the rigid shin cuff is attached at a back portion to a shin cuff strap.

8. The offset double upright knee brace of claim 1, wherein a calf strap is attached at each end to the medial and lateral upright member integral with the rigid shin cuff.

9. The offset double upright knee brace of claim 2, wherein there are three blocks supporting the elastic band.

10. An offset double upright knee orthosis for treating osteoarthritis of a knee joint comprising:
   a polycentric hinge on one side of the knee joint affected by osteoarthritis;
   a unicentric hinge on a second side of the knee joint affected by osteoarthritis;
   the polycentric hinge attached at a lower portion to an upright member integral with a rigid shin cuff adapted to be circumscribable about an anterior portion of a lower leg of a patient and attached with an upper arm to a thigh cuff adapted to be aligned with a back of a patient's thigh;
   the polycentric hinge having a central slotted plate with an upper star gear rigidly attached to a back of the slotted plate, a second star gear movably attached at the back of the slotted plate by a rivet, multiple threaded holes spaced apart adjacent a front edge of the slotted plate, corresponding blocks insertable in the threaded holes with an elastic band positioned on a front portion of the blocks with a lower and upper fulcrum point terminating ends of the elastic band on an outside surface of the polycentric hinge;
   the unicentric hinge having an upper arm attached to the thigh cuff, the upper arm of the unicentric hinge being longer than the upper arm of the polycentric hinge, the unicentric hinge having a lower arm attached to an integral upright member of the rigid shin cuff around the lower leg, the unicentric hinge having an extension and a flexion setting on a central plate;
   the second upright member integral with the rigid shin cuff, the polycentric hinge and the upper arm of the lateral polycentric hinge all defining a first upright of the knee orthosis;
   the first integral upright member of the rigid shin cuff around the lower leg, the medial hinge bottom end, the unicentric hinge and the upper arm of the medial unicentric hinge all defining a second upright of the knee orthosis; and
   the brace offset configuration resulting from the semi-rigid thigh cuff having one side positioned at a height higher than its opposed side, such that the semi-rigid thigh cuff and the rigid shin cuff have different horizontal axis and wherein the upper arm of the unicentric hinge is angled backwardly from a vertical axis of the second medial upright.

11. The offset double upright knee orthosis of claim 10, wherein there are one to four blocks supporting the elastic band.

12. The offset double upright knee orthosis of claim 10, wherein the upper arm of the unicentric hinge is at least 1½ inches longer than the upper arm of the polycentric hinge.

13. The offset double upright knee orthosis of claim 10, wherein there are three blocks supporting the elastic band.

14. The offset double upright knee orthosis of claim 10, wherein the thigh cuff is attached to a thigh cuff securing strap and the rigid cuff around the lower leg is attached at a back portion to a shin cuff strap.

15. An offset double upright knee orthosis for treating osteoarthritis of a knee joint comprising;
   a unicentric hinge on one side of the knee joint affected by osteoarthritis and a polycentric hinge on a second side of the knee joint affected by osteoarthritis;
   the unicentric hinge having an upper arm attached to a thigh cuff adapted to circumscribe about a posterior potion of a thigh of a patient, a lower arm attached to a knee ring adapted to circumscribe about an anterior portion of a lower leg of a patient and a central plate containing an extension and a flexion setting, the upper arm having a 15° to 20° set back angle with the patient's leg straight;
   the polycentric hinge attached at a lower portion to the knee ring and with an upper arm to the thigh cuff, the polycentric hinge having a slotted plate between the lower portion and upper arm, an upper first star gear rigidly attached to a back of the slotted plate, a second star gear movably attached at the back of the plate by a transverse shaft through the slot, multiple threaded holes spaced apart and adjacent at a front edge of the slotted plate, corresponding blocks insertable in the threaded holes with an elastic band positioned on a front portion of the blocks with a lower and upper fulcrum point terminating ends of the elastic band on an outside surface of the polycentric hinge;
   the upper arm of the unicentric hinge having a length greater than the length of the upper arm of the polycentric hinge;
   the polycentric hinge lower portion, the polycentric hinge and the polycentric upper arm all defining a first upright of the knee orthosis;
   the unicentric hinge upper arm, the unicentric hinge and the unicentric hinge lower arm all defining a second upright of the knee orthosis; and
   the brace offset configuration resulting from the semi-rigid thigh cuff having one side positioned at a height higher than its opposed side, such that the semi-rigid thigh cuff and the rigid shin cuff have different horizontal axis and wherein the upper arm of the unicentric hinge is angled backwardly from a vertical axis of the second medial upright.

16. The offset double upright knee orthosis according to claim 15, wherein there are four threaded holes in the slotted plate.

17. The offset double upright knee orthosis according to claim 15, wherein there are one to four blocks supporting the elastic band.

18. The offset double upright knee orthosis according to claim 17, wherein there are three blocks supporting the elastic band.

19. The offset double upright knee orthosis according to claim 15, wherein the upper arm of the unicentric hinge is at least 1½ inches longer than the upper arm of the polycentric hinge.

20. The offset double upright knee orthosis according to claim 15, wherein the thigh cuff is attached to a thigh cuff securing strap and the knee ring around the lower leg is attached at a back portion to a shin cuff strap.

* * * * *